United States Patent
Peligrad et al.

(10) Patent No.: US 8,617,072 B2
(45) Date of Patent: Dec. 31, 2013

(54) SYSTEM FOR THE NONINVASIVE DETERMINATION OF TRACER CONCENTRATION IN BLOOD

(75) Inventors: Dragos-Nicolae Peligrad, Aachen (DE); Lothar Spies, Aachen (DE); Timo Paulus, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 1193 days.

(21) Appl. No.: 11/569,437

(22) PCT Filed: May 20, 2005

(86) PCT No.: PCT/IB2005/051645
§ 371 (c)(1),
(2), (4) Date: Aug. 17, 2007

(87) PCT Pub. No.: WO2005/116902
PCT Pub. Date: Dec. 8, 2005

(65) Prior Publication Data
US 2011/0060205 A1 Mar. 10, 2011

(30) Foreign Application Priority Data
May 28, 2004 (EP) .................................. 04102395

(51) Int. Cl.
*A61B 5/00* (2006.01)

(52) U.S. Cl.
USPC ........... 600/368; 600/407; 600/420; 600/425; 600/431; 600/435; 600/458; 600/500; 600/504; 382/128; 382/133; 382/134

(58) Field of Classification Search
USPC ......... 600/368, 500–504, 407, 425, 431–435, 600/420, 458; 702/25; 328/128, 133, 134
See application file for complete search history.

(56) References Cited

U.S. PATENT DOCUMENTS

| | | | |
|---|---|---|---|
| 6,055,985 A * | 5/2000 | Bae et al. | 604/28 |
| 6,470,889 B1 * | 10/2002 | Bae et al. | 604/28 |
| 6,631,291 B2 * | 10/2003 | Viertio-Oja et al. | 600/544 |
| 2002/0013662 A1 * | 1/2002 | Grass et al. | 702/19 |

(Continued)

FOREIGN PATENT DOCUMENTS

JP  61173496  8/1986

OTHER PUBLICATIONS

Calamante et al. ,Quantification of Bolus-Tracking MRI: Improved Characterization of the Tissue Residue Function Using Tikhonov Regularization, Magnetic Resonance in Medicine 50:1237-1247, 2003.*

(Continued)

*Primary Examiner* — Christine Matthews
*Assistant Examiner* — Sunita Reddy (57) ABSTRACT

The invention relates to a general composite compartmental model and a compartmental analysis procedure to extract non-invasively the concentration ($C_p$) of the imaging agent in plasma (301), in metabolites (304, 504) and in blood elements (303) (like red cells, platelets, plasma protein etc.) from time signal curves measured within a reference tissue region (200). This is made possible by deploying an injection function ($S_{INJ}(t)$) as input which models the amount of imaging agent administered to the patient as a function of time. The invention allows the presentation of the plasma input function to the medical practitioner without the need for invasively drawing blood samples.

18 Claims, 3 Drawing Sheets

(56) References Cited

U.S. PATENT DOCUMENTS

| | | | |
|---|---|---|---|
| 2003/0191377 A1* | 10/2003 | Robinson et al. | 600/310 |
| 2003/0211036 A1* | 11/2003 | Degani et al. | 424/1.11 |
| 2004/0122702 A1* | 6/2004 | Sabol et al. | 705/2 |
| 2004/0153139 A1* | 8/2004 | Altman | 623/1.15 |
| 2004/0242994 A1* | 12/2004 | Brady et al. | 600/420 |

OTHER PUBLICATIONS

Perlmutter et al., Strategies for In Vivo Measurement of Receptor Binding Using Positron Emission Tomography, J Cereb Blood Flow Metab, vol. 6, No. 2, 1986, pp. 154-169.*

Huang et al. (Modelling approach for separating blood time-activity curves in positron emission tomographic studies, Phys. Med. Biol., 1991, vol. 36, No. 6, pp. 749-761).*

Brix et al: "Regional Blood Flow, Capillary Permeability, and Compartmental Volumes: Measurement With Dynamic CT-Initial Experience"; Radiology, vol. 210, No. 1, Jan. 1999, pp. 269-276, XP002380243.

Upton et al: "The Two-Compartmental Recirculatory Pharmacokinetic Model-An Introduction to Recirculatory Pharmacokinetic Concepts"; British Journal of Anaeesthesia, vol. 92, No. 4, Apr. 2004, pp. 475-484, XP002380244.

Narayana et al: Construction of a Whole Body Blood Flow Model for Use in Positron Emission Tomography Imaging With [150] Water.

Mayr et al: "Estimating Kinetic Parameters From Dynamic Contrast-Enhanced T1-Weighted MRI of a Diffusable Tracer: Standardized Quantities and Symbols"; Journal of Magnetic Resonance Imaging, vol. 10, No. 3, Sep. 1999, pp. 223-232, XP002380246.

Ichise et al: "An Introduction to Pet and Spect Neuroreceptor Quantification Models"; Journal of Nuclear Medicine, vol. 42, No. 5, May 2001, pp. 775-763, XP002362257.

Huang et al: "Modelling Approach for Separating Blood Time-Activity Curves in Positron Emission Tomographic Studies"; Physics in Medicine and Biology, vol. 36, No. 6, 1991, pp. 749-761, XP002362258.

Perlmutter et al: "Strategies for In-Vivo Measurement of Receptor Binding Using Positron Emission Tomography"; Journal of Cerebral Blood Flow and Metabolism, vol. 6, No. 2, 1986, pp. 154-169, XP009059763.

Huang et al: "Principles of Tracer Kinetic Modeling in Positron Emission Tomography and Autoradiography"; Positron Emission Tomography and Autoradiography: Principles and Applicagtions for the Brain and Heart, pp. 287-346, Raven Press, 1986.

* cited by examiner

SYSTEM FOR THE NONINVASIVE DETERMINATION OF TRACER CONCENTRATION IN BLOOD

The invention relates to data processing systems and a method for the evaluation of image data that represent the concentration of at least one imaging agent in a body volume, to record carriers on which a computer program for such an evaluation is stored, and an examination apparatus with said data processing system.

When using medical imaging devices such as CT (Computed Tomography), MR (Magnetic Resonance), PET (Positron Emission Tomography), SPECT (Single Photon Emission Computed Tomography) or US (Ultrasound) systems to display functional or morphological properties of a patient under study, either a number of static scans or a contiguous time series of dynamic scans is recorded. To obtain the medical information of interest encoded in these images in certain applications a compartmental analysis of the underlying chemical, biological and physiological processes has to be accomplished. Compartmental analysis is based on a special type of mathematical model for the description of the observed data, in which physiologically separate pools of an imaging agent (also called tracer substance) are defined as "compartments". The model then describes the concentration of said imaging agent in the different compartments, for example in the compartment of arterial blood on the one hand side and in the compartment of tissue on the other hand side (it should be noted, however, that in general compartments need not be spatially compact or connected). Typically, there is an exchange of substance between the various compartments that is governed by differential equations with (unknown) parameters like exchange rates. In order to evaluate a compartment model for a given observation, the differential equations have to be solved and their parameters have to be estimated such that the resulting solutions optimally fit to the observed data. More details on the technique of compartmental analysis may be found in the literature (e.g. S. Huang and M. Phelps, "Principles of Tracer Kinetic Modeling in Positron Emission Tomography and Autoradiography" in: M. Phelps, J. Mazziotta, and H. Schelbert (eds.), Positron Emission Tomography and Autoradiography: Principles and Applications for the Brain and Heart, pp 287-346, Raven Press, New York, 1986).

In dynamic compartmental analysis the so-called "(plasma) input function" defines the amount of imaging agent (free and/or metabolized) within the blood which can go into the tissue. It cannot be easily determined non-invasively. In order to circumvent the need to measure the input function invasively (by drawing venous or arterial blood samples), the dynamic analysis sometimes utilizes the reference tissue concept, wherein the total time signal curves (TSC) are detected in two different tissue regions (VOIs) called "reference tissue" and "target tissue" (cf. J. S. Perlmutter, K. B. Larson, M. E. Raichle, J. Markham, M. A. Mintum, M. R. Kilbourn, M. J. Welch: "Strategies for In Vivo Measurement of Receptor Binding using Positron Emission Tomography", J. Cereb. Blood Flow Metab. 6, (1986) pp 154-169; M. Ichise, J. H. Meyer, Y. Yonekura: "An Introduction to PET and SPECT Neuroreceptor Quantification Models", Jour. of Nucl. Med. 42, (2001) pp 755-763 with more references). For this concept it is assumed that the input function to both tissues (reference and target) is the same. Furthermore, the following assumptions need to be imposed: Firstly, no metabolic products are produced within the tissues which may get washed out, and secondly, metabolic products cannot penetrate the blood-tissue barrier. Thus since the input function is substituted by the time signal curve (TSC) of the reference tissue, the reference tissue TSC will act as a "filter" for the metabolic products within blood. Nevertheless all these assumptions are legitimate only if the fractional blood volume within the observed region is negligible small, and if there is no binding (within the tissue of interest, red cells, platelets or plasma protein) of the imaging agent in the reference region and additionally if no penetration of the metabolic products through the blood-tissue barrier is possible. Due to the limited spatial resolution of the PET scanners, however, VOIs may in practice contain not only tissue but also blood elements and metabolites, which can in general penetrate the blood-tissue barrier. Both the amount of free (unmetabolized) imaging agent and labeled metabolites in plasma can be assayed directly from samples of blood taken throughout the detection (scan) whereas the contribution of labeled metabolites to the tissue signal cannot be measured directly. All this may contaminate the results derived with state-of-the-art techniques, which suffer from the limitations just mentioned.

Based on this situation it was an object of the present invention to provide means for a more realistic evaluation of image data without the need for an invasive determination of the plasma input function.

This object is achieved by methods, systems and computer readable media according to the various appended claims.

A data processing system according to a first aspect of the present invention serves for the evaluation of image data that represent the concentration of at least one imaging agent in a body volume. The image data may for example be PET scans that represent the spatial distribution of a radioactive imaging agent. The data processing system may particularly be realized by a microcomputer comprising usual components like (volatile or nonvolatile) memory, processors, I/O interfaces and the like together with the necessary software. The data processing system is adapted to estimate the distribution of the imaging agent in blood or parts thereof (e.g. plasma, blood elements) from a measured injection function that describes the injection of the imaging agent into the body. Said injection function may for example be expressed by the volume flow of imaging agent through a syringe or an infusion system into the veins of a patient.

For the evaluation of compartment models it is necessary to know the concentration of the imaging agent in blood, i.e. the plasma input function. This concentration is normally measured invasively by drawing blood samples from the patient at different times, a procedure which is both laborious for the medical staff and troublesome for the patient. The data processing system proposed above avoids such problems by taking the injection function as information from which the distribution of the imaging agent in blood is calculated. The injection of the imaging agent is a necessary prerequisite of the investigation, and therefore the measurement of the injection function means no additional strain for the patient. Details on how the distribution of the imaging agent is calculated from the injection function will be described below in connection with preferred embodiments of the invention.

According to a second aspect, the invention comprises a data processing system for the evaluation of image data that represent the concentration of at least one imaging agent in a body volume, wherein said data processing system is adapted to evaluate a reference region based on a compartment model, and wherein the reference region comprises both blood and reference tissue as subsystems. Preferably, the data processing system is additionally designed according to the first aspect of the invention, i.e. it may use a measured injection function for the estimation of the distribution of the imaging agent in blood.

As explained above, approaches are known from literature which use a reference tissue for the determination of certain parameters that are needed for the evaluation of a target tissue. These approaches are however based on special assumptions, particularly on the neglect of the contribution of blood present in a reference region to the measured signal. In contrast to this, the aforementioned data processing system explicitly considers blood as a subsystem in the reference region, which allows for much more precise and realistic modeling of the reference region.

According to a further development of the invention, the data processing system (according to the first and particularly to the second aspect) is adapted to calculate the plasma input function, i.e. the concentration of the imaging agent in blood plasma, during the evaluation of the reference region. Compared to the determination of the plasma input function from blood samples, this offers the advantage to be noninvasively and to represent the conditions at close proximity to a target region.

Moreover, the compartment model of the reference region may optionally comprise at least one compartment that represents metabolites of the imaging agent in blood and/or at least one compartment that represents metabolites of the imaging agent in the reference tissue. Metabolites of the imaging agent are produced for example by blood cells, organs, or in the reference tissue. The metabolites contribute to the measured signals, for example the measured radioactive decay of tracer atoms, but they have a different physiological behavior and are typically no longer available for the specific binding processes that shall be investigated by the imaging agent. The knowledge of the amount of metabolites is therefore a valuable information needed for a correct quantification of the free imaging agent.

The compartment model of the reference region may further comprise at least one compartment representing the binding of imaging agent in blood elements like blood cells and/or at least one compartment representing the binding of imaging agent in the reference tissue. Imaging agent that is bound in blood elements or in the reference tissue is lost for the specific processes that shall be observed while still contributing to the measured signals. Therefore, the knowledge of the amounts of agent that are bound is required for a more precise evaluation of the physiological processes.

The data processing system may furthermore be adapted to evaluate a target region in which the imaging agent is specifically bound, the evaluation being based on information obtained from the reference region. If possible, the reference region is chosen such that it differs only in the specific features to be investigated from the target region.

According to a further development of the invention, the data processing system is adapted to calculate errors that are associated with the evaluation of the image data based on different compartment models. Thus, various compartment models with for example different numbers of compartments may be applied to the measured image data and evaluated with respect to said error. A comparison of the resulting errors then allows to select a model that seems to be most appropriate for the description of the measurements.

The processing system may particularly comprise a display unit on which the results of the evaluation procedures may be displayed. The graphical display of the available information (time signal curves, parametric maps, morphological information etc.) is an important aspect of the data processing system as it allows a physician a fast, intuitive access to the available information.

The invention further comprises a record carrier, for example a floppy disk, a hard disk, or a compact disc (CD), on which a computer program for the evaluation of image data that represent the time varying concentration of at least one imaging agent in an object is stored, wherein said program is adapted to estimate the distribution of the imaging agent in blood of parts thereof from a measured injection function that describes the injection of the imaging agent into the body.

Moreover, the invention comprises a record carrier on which a computer program for the evaluation of image data that represent the time varying concentration of at least one tracer substance in an object is stored, wherein said program is adapted to evaluate a compartment model of a reference region, the reference region comprising blood and reference tissue as subsystems.

Furthermore, the invention comprises an examination apparatus with an imaging device for generating image data that represent the time varying concentration of at least one imaging agent in an object, and a data processing system of the kind described above. The imaging device may for example be a PET, SPECT, CT, MR, or US system.

The invention also comprises a method for the evaluation of image data that represent the concentration of at least one imaging agent in a body volume, comprising the estimation of the distribution of the imaging agent in blood or parts thereof from a measured injection function that describes the injection of the imaging agent into the body.

Finally, the invention comprises a method for the evaluation of image data that represent the concentration of at least one imaging agent in a body volume, comprising evaluation of a compartment model of a reference region, the reference region comprising blood and reference tissue as subsystems.

The aforementioned record carriers, methods and examination apparatus rely on the features of a data processing system as it was described above. For more information on details, advantages and further developments of the record carriers, methods and the examination apparatus, reference is therefore made to the description of the data processing system.

These and other aspects of the invention will be apparent from and elucidated with reference to the embodiment(s) described hereinafter.

In the following the invention is described by way of example with the help of the accompanying drawings in which.

In the following a compartmental analysis and quantification of a reference region based on a composite (compartmental) reference tissue model will be described that is suitable for clinical studies and that takes all shortcomings previously mentioned into account: fractional blood volume, metabolites that cross the blood-tissue barrier and/or other unspecific binding sources within the target tissues. To take advantage of the maximal resolution which the imaging devices can supply, this analysis has to be done on a per-voxel basis. In order to perform the full dynamic analysis a set of assumptions and concepts are introduced and discussed below.

The basic idea is to propose a general composite compartmental model (topology) and a compartmental analysis procedure to extract non-invasively the concentration of the free imaging agent in plasma (FIAP), the concentration of the imaging agent in metabolites and the concentration of the imaging agent in blood elements (like red cells, platelets, plasma protein etc.) from time signal curves measured within a reference region. This is made possible by deploying an "injection function" $S_{INJ}$ as input (panel 100) to the compartmental analysis. The injection function models the amount of imaging agent administered to the patient as a function of time. This function is determined by the clinical protocol and for example expressed as the flow of imaging agent (ml/s) leaving a syringe.

Figure 1:
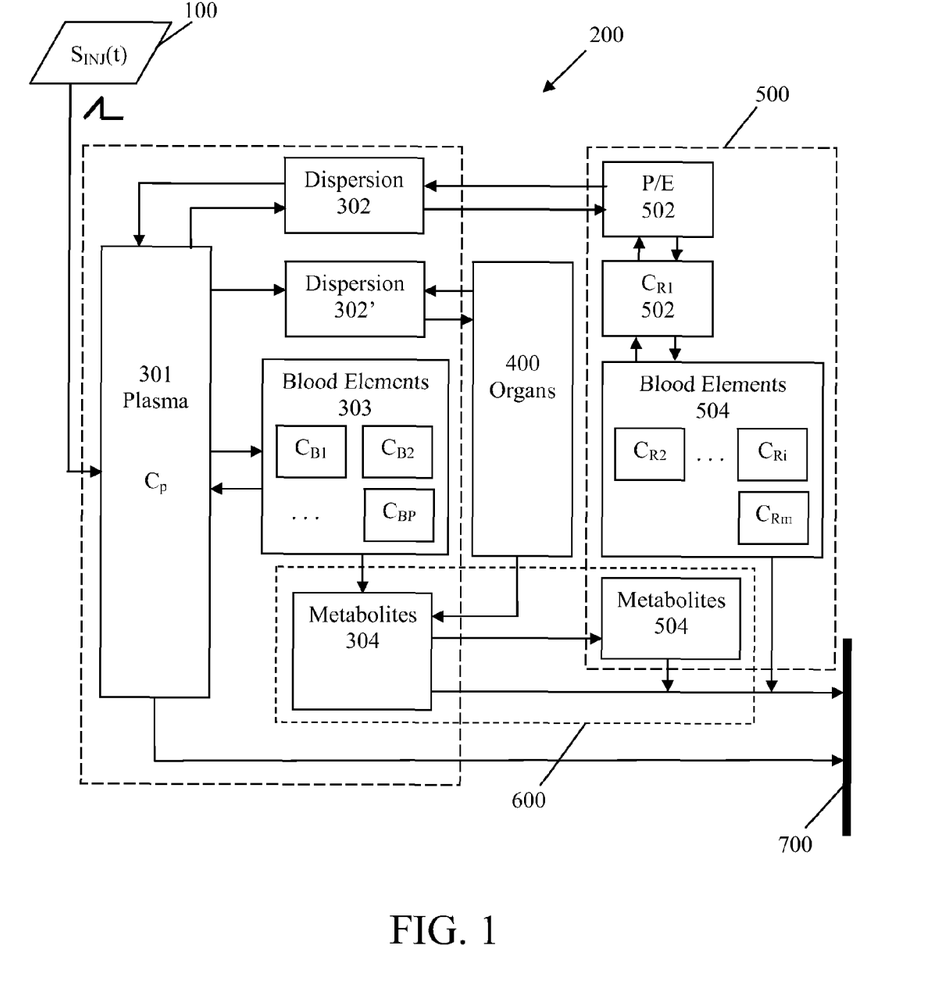
FIG. 1 shows a compartment model of the reference region according to the present invention.

The proposed composite reference tissue (CRT) model contains subsystems which have compartments that account for the amount of imaging agent distributed in the reference region 200 or volume of interest (VOI) either as free (unmetabolized) in the plasma, or bound in tissue, blood elements, metabolites and/or other trapping sources within the VOIs under study (see FIG. 1).

The proposed compartmental analysis procedure comprises a dynamic analysis of the reference region 200 VOI using the injection function $S_{INJ}$ as input in order to extract the local free (unmetabolized) imaging agent concentration in plasma by decomposition of the total time signal curves. The procedure is applicable to either the complete set of recorded images (either several static scans or the 4-dim. time-scan data based on a VOI analysis, images which can be reconstructed images from a PET, SPECT, MRI or US scanner) and which generates from the input maps of all the relevant chemical, biological and physiological parameters on a per-voxel basis.

The following concepts and definitions are used in the embodiment to be described:

It will be distinguished between specific or nonspecific binding of the labeled imaging agent within either diffusible ("delocalized") or non-diffusible ("localized") binding sites. Here specific binding means targeted binding (the kind of binding that shall be investigated) whereas the nonspecific binding will contribute to the "background" considered as the total amount of detectable imaging agent which does not participate in the specific binding process. For the sake of generality the labeled imaging agent should not be considered always as detectable in order to include also the smart imaging agents. Often the binding process is the metabolization of the imaging agent within the blood or tissues under study. The labeled metabolized imaging agent binds either specifically or unspecifically to non-diffusible binding sites (tissue or blood elements like red cells, platelets, plasma protein etc.) or to diffusible binding sites which can freely circulate the entire body as labeled metabolites.

In the "non-specific binding" subsystems (regions) within the VOI the imaging agent can flow freely directly or indirectly from plasma into these regions, move freely among compartments of these subsystems, and, in turn, flow back into the plasma. These subsystems are called reversible since the imaging agent transfer between and among the plasma and those subsystems is fully reversible. Usually the imaging agent in the unspecific binding subsystems (regions) leaves this part of the system by going into either the plasma (if unmetabolized) or (if metabolized) into other subsystems which can be freely diffusible and/or act as specific binding sites.

A special case is when the in- and efflux are equal over the detection time frame such that the amount of circulated imaging agent is conserved. In this case the imaging agent is absent at both the initial moment and the end of the detection. Such regions are called "free" or "loss-less" since the imaging agent returns unchanged in the plasma. For sake of completeness one should mention that the unspecific binding tissue regions may not rapidly equilibrate with the regions where the imaging agent is free as usually assumed. Usually the transfer processes of the imaging agent within the system obeys first-order linear or nonlinear kinetics.

The "specific binding" subsystems (regions) within the VOI are called irreversible since the imaging agent after entering this region from the plasma and/or reversible tissue regions cannot leave the binding site within the detection time frame, neither back to plasma nor to the reversible tissue regions.

In the "trapping" subsystems (regions) within the VOI, also called "lossy", the labeled imaging agent can flow-in freely directly or indirectly from plasma but cannot flow back into the plasma since it will be irreversible non-specifically bound within these subsystems. Furthermore the "trapping sources" may not be—but are often—freely diffusible, i.e. they can circulate the entire body, can flow in and out and/or move freely among reversible subsystems other then the trapping one. Therefore the signal measured from these "lossy" tissue regions will contribute also to the overall detection (total tissue signal) and in most of the cases it will contaminate the signal detected from the specific binding of imaging agent in the target tissue.

The following general assumptions are made for the transport model illustrated in FIG. 1:

Assumptions for the Imaging Agent:
i. The imaging agent, which may for example be F-MISO (F-Fluoromisonidazole), is assumed to be delivered via arterial blood flow to the blood 300 and transported into tissue by active/mediated transport diffusion. There is a single source, namely the free imaging agent in the plasma 301, its concentration being denoted as $C_p$.

ii. The imaging agent does not perturb (alter) the system and is not initially present in the tissue regions (either reversible or irreversible).

iii. The extraction fraction of the free imaging agent from plasma into tissue is not necessarily small and thus the rate of transport to tissue can be dependent on blood flow (see panel 502 "Perfusion/Extraction"). For the sake of generality also the dispersion representing the different "biochemical" distances needed for the free imaging agent from the moment of injection until it starts supplying the target and reference tissue should be considered (see panels 302, 302' "Dispersion").

Assumptions for the Role of Labeled Metabolites within the System:
iv. As already mentioned one of the major problems in the quantitative interpretation of dynamic scans is the presence of detectable labeled metabolites. In this example it will be assumed that all labeled metabolites formed in the system under study are detectable and contribute to the total tissue signal in the sense of a contamination of the data. Labeled metabolites in tissue may result either from the metabolism of the free imaging agent within the blood elements and tissues under study or be taken up from the blood during the detection (scan). It is possible to extend this analysis also for cases where various types of metabolites are labeled with different types of imaging agents in order to distinguish their contribution to the total tissue signal. In this case a separate detection using multiple scans is necessary (cf. S. C. Huang, J. R. Barrio, D. C. Yu, B. Chen, S. Grafton, W. P. Melega, J. M. Hoffman, N. Satyamurthy, J. C. Mazziotta, M. E. Phelps: "Modelling approach for separating blood time-activity curves in positron emission tomographic studies", Phys. Med. Biol., 36, (1991) pp 749-761). In such cases the actual procedure for analysis should be applied for each type of imaging agent separately.

Most of the metabolites in the blood supplying the tissue (see panel 304 "Metabolites in Blood") are either due to the peripheral metabolism (see panel 400 "Organs") or blood metabolism of the free imaging agent (panel 303 "Blood Elements"). In blood there may also be an uptake of metabolites formed from the free imaging agent passing through either interstitial or intracellular space within the tissue of study. As stated earlier, one distinguishes between the metabolized imaging agent either specifically bound to target binding sites or non-specifically bound to diffusible and/or non-diffusible binding sites within the VOI. The detectable metabolized imaging agent bound to diffusible binding sites leaves the tissue regions and flows back into the blood but it is no longer available as free imaging agent for further possible metabolization processes, i.e. it can penetrate the blood-tissue barrier again only as metabolites. Thus for the sake of generality one can consider as "metabolites" all the trapping sources of the system under study, i.e. the amount of imaging agent irreversible and non-specifically bound within the VOI. In conclusion the role of metabolites within the system can be described by an appropriate trapping subsystem (see dashed panel 600 "Metabolites") which can contain one or more compartments (e.g. within blood, tissue or reference tissue) which can be mathematically lumped together in a common metabolite pool if the assumption is valid that the metabolites produced within tissues (interstitial or intracellular for target and reference tissue) or in blood elements will exchange rapidly with the metabolites in the blood. Metabolites (as well as free imaging agent from 301) may leave the body permanently to the "Exit" 700.

v. In this example the case is considered that the metabolites within the blood can penetrate through the blood-tissue barrier in any kind of tissue regions, containing any kind (specific and/or nonspecific) of binding sites.

vi. Moreover, the clearance of the labeled metabolites out of the body either from the blood metabolite pool or directly from the tissues under study is considered.

Assumptions for the Labeled Blood Elements in the VOI:

vii. The blood elements consist of a subsystem having compartments which communicate reversibly only with the free imaging agent in the plasma (see panel 303 "Blood Elements"). The reversible communication with the plasma can occur directly or indirectly through intermediary compartments which can all be mathematically lumped together only if they rapidly equilibrate during detection of the amount of free imaging agent in plasma. It will be assumed in this example that all the labeled blood elements within the blood are detectable and contribute to the total tissue signal in the sense of a contamination of the data.

viii. The blood elements can metabolize the free imaging agent within the blood as mentioned already.

ix. The blood elements cannot pass the blood tissue barrier and should not be allowed to diffuse into the tissue regions of the VOI.

Assumptions for the Reference Tissue 500:

x. The reference tissue 500 may consist of a number of subsystems each of them having compartments which communicate reversibly with the free imaging agent in the plasma, including compartments 501 (e.g. interstitial), 503 (e.g. blood elements) and 504 (e.g. metabolites). This reversible communication with the plasma can occur directly or indirectly through intermediary compartments. There is at least one compartment 501 (e.g. the interstitial) in which the imaging agent within the tissue is considered as "free". This compartment can be mathematically lumped together with other nonspecific binding compartments if the amount of transferred imaging agent between the compartments rapidly equilibrates during detection. The interstitial compartment models the properties of the tissue membrane.

xi. The reference tissue 500 is not specifically binding the imaging agent; therefore it should not contain any irreversible subsystems.

xii. All types of metabolites can flow in and out of the reference tissue 500 but they cannot be irreversible bound within. Also no metabolization of the free imaging agent within the reference tissue should be allowed. Thus a free movement of the metabolites among all reversible subsystems other than the interstitial ones is not allowed (i.e. the metabolites subsystem has no exchange with any other reversible subsystem except the interstitial one).

xiii. Finally, no oscillation of the free imaging agent within the entire system under study should be mathematically allowed since such oscillatory processes are physiologically extremely improbable.

In order to achieve a minimum of contamination and thus reliable quantification the best candidates for the reference tissue are therefore homogeneous regions where the vascularization and nonspecific binding of the imaging agent within it are minimal.

In order to accurately estimate the dynamic parameters (e.g. binding rate) of the imaging agent kinetics within the reference region VOI the system of ordinary differential equations (ODE) associated to a given topology of the CRT model is evaluated using appropriate boundary conditions. These can be information about the initial values of the concentrations of the imaging agent within each of the compartments or the amount of unmetabolized imaging agent still present at a given moment of time during the scan. If solved analytically the solution of the system of ODE gives the total time signal curve which then can be used to obtain the simulated detection time signal given by:

$$S(t) = \{V_B([1-(\alpha+\beta)]C_p(t) + \alpha G_B(t) + \beta G_{MB}(t)) + V_T \gamma G_{MT}(t) + V_T G_T(t)\} \otimes S_{INJ}(t) \quad (1)$$

Here $C_p(t)$ is the concentration of free imaging agent in the plasma (FIAP), $S_{INJ}(t)$ is the injection function of the agent in the blood, $G_T$, $G_{MT}(t)$ are the impulse-response functions of the tissue and metabolites subsystems within the reference tissue volume fraction $V_T$ whereas $G_B(t)$, $G_{MB}(t)$ represent the impulse-response of the blood elements and metabolites subsystems within the blood volume fraction $V_B$ of the same reference region VOI. $\alpha$ and $\beta$ are the partial volume fractions of the blood elements and the metabolites, respectively, within the blood subsystem and in the appropriate target and/or reference tissue ROI. Similarly $\gamma$ is the partial volume fraction of the metabolites within the target and/or reference tissue ROI. Subscripts T stands for "tissue", B for "blood", MB for metabolites within blood, MT for metabolites within tissue. The tissue volume fraction $V_T$ may comprise both interstitial and intracellular volume fractions. The impulse-response functions are the solution of a system of ODE associated to a compartmental topology particularly considered (as in FIG. 1), where the $\delta(t)$-function is taken as input. Thus the FIAP time signal: $S_p(t) = V_B[1-(\alpha+\beta)]C_p(t) \otimes S_{INJ}(t)$ is obtained by decomposition of the total time signal into components, namely besides FIAP also the amount of trapped imaging agent in metabolites: $S_M(t) = [V_B \beta G_{MB}(t) + V_T \gamma G_{MT}$ (t)]⊗$S_{INJ}$ and the amount of imaging agent within the non-specific binding subsystems of the reference region VOI including the blood fractional volume: $S_{TB}(t)=[V_B G_B(t)+V_T G_T(t)]\otimes S_{INJ}(t)$. This decomposition can be performed only if the assumptions that there is neither specific binding nor metabolization of the imaging agent within the reference region are valid. Finally it permits to identify the compartmental topology of the tissues under study and thus to determine reliable the dynamic parameters from the model parameters for a given topology.

Figure 2:
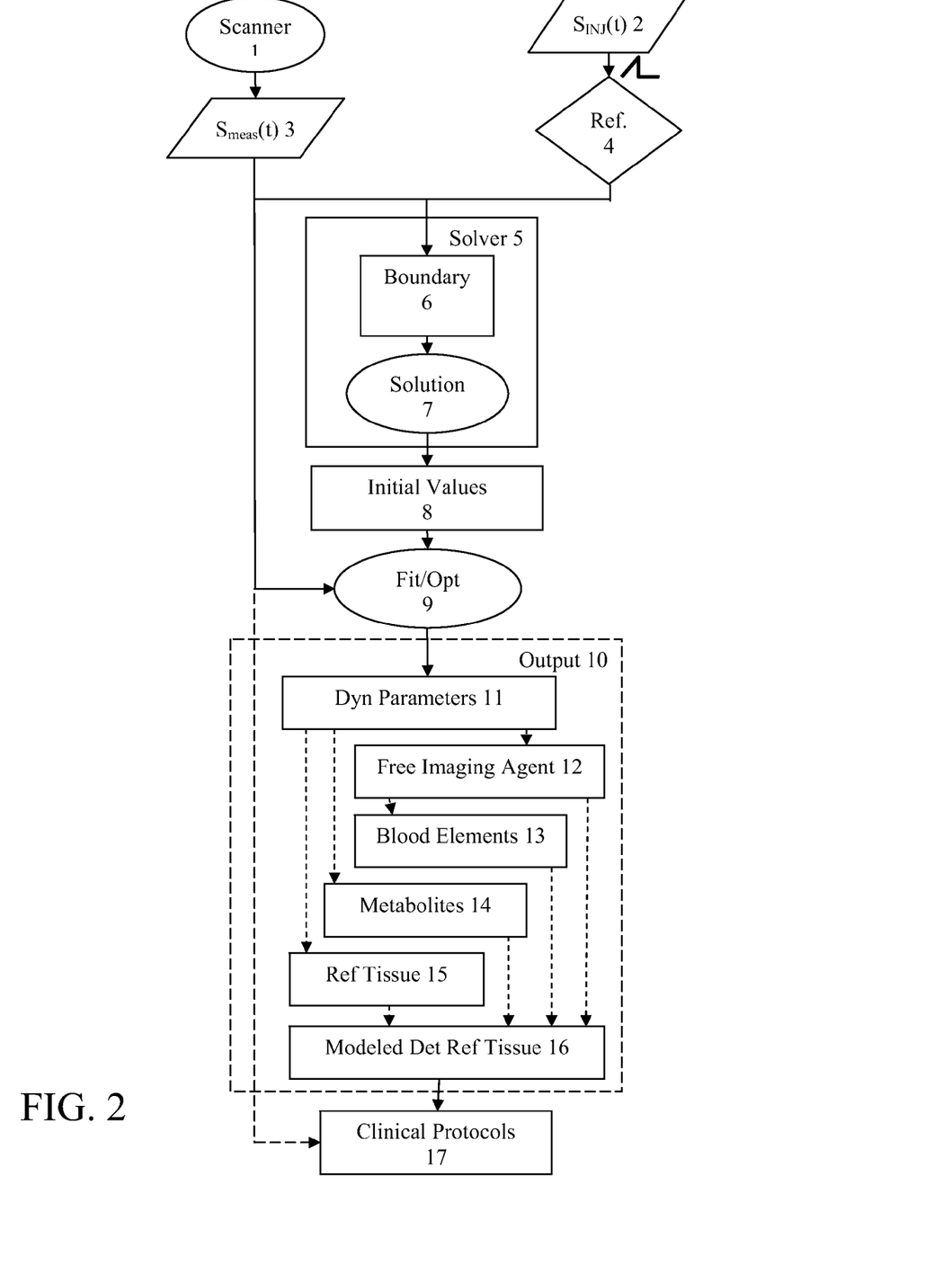
FIG. 2 is a flowchart of the kinetic analysis of the reference region according to the present invention.
Figure 3:
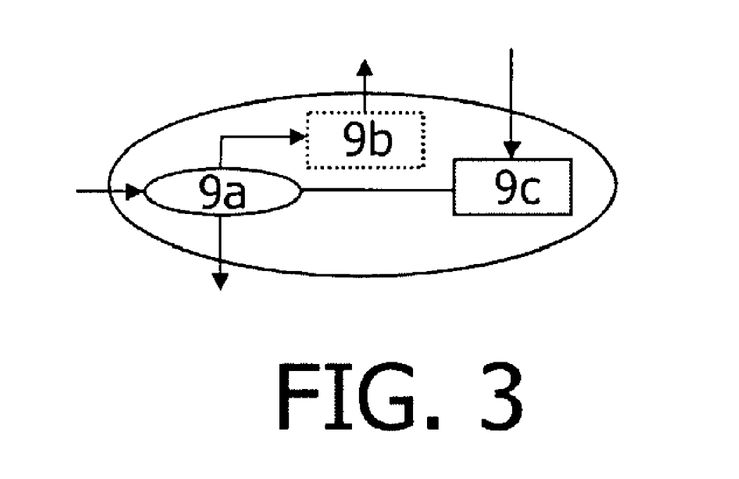
FIG. 3 is a particular embodiment of the "Fit and Optimization" block of FIG. 2.

The general kinetic analysis for the reference region VOI is achieved by the following procedure according to the flowcharts of FIGS. 2 and 3:
1. Data acquisition: Readout of the input data (dynamic time series $S_{meas}(t)$ from reference region VOI) from the medical imaging device (e.g. a PET scanner 1).
2. Selection of the appropriate compartmental topology for the CRT model in order to perform the dynamic analysis based on the injection function $S_{INJ}(t)$ from block 2. This is visualized in the flowchart of FIG. 2 as follows:
   a. First a compartmental topology is selected from a list containing multiple alternatives (panel 4 "Ref. Tissue Compartmental Model").
   b. Then the model parameters have to be specified (see panel 8 "Initial Values") and the underlying system of differential equations associated to the selected compartmental model have to be solved analytically or numerically (panel 5 SOLVER) using appropriate boundary conditions (panel 6 "Boundary Condition" and panel 7 "Analytical or Numerical Solution of S-ODE's and of Jacobian"). The analytical solution—if existing—is selected from a predefined list containing all analytical solutions for the compartmental topologies considered in the library of CRT panel 4.
3. The simulated total time signal is then fitted to the data (see panel 9 "Nonlinear Fit/Optimization") in order to obtain an optimized solution with respect to the relevant parameters (specified under 2). A particular embodiment of the "Nonlinear fit and/or Optimization" is shown in FIG. 3. The optimization method should be a weighted least squares nonlinear fit of the calculated total time signal S(t) to the input data $S_{meas}(t)$ from the same VOI. The appropriate algorithm is selected from a list of various alternative algorithms like Levenberg-Marquard, Gauss-Newton, Simplex etc. (see panels 9a "Nonlinear-Fit/Optimization", 9b "New initial values for dynamic parameters", 9c "Simulated Signal" in FIG. 3). The dynamic parameters have to be optimized in order to become independent of their initial values. Appropriate criteria for optimization like $\chi^2/d.o.f.$, Akaike- and/or F-test, etc. should be available for selection from a dedicated library. In order to refine the numerical analysis the compartmental topology of the system under study can be also numerically determined (identified). In this case various compartmental topologies are analyzed in order to obtain for the error estimation of the dynamic parameters the best score for appropriate test algorithms as for e.g. to minimize $\chi^2/d.o.f.$
4. At the end of the flowchart (cf. FIG. 2, panel 10 "OUTPUT") all the dynamic parameters are determined (for the optimum compartmental topology) and the simulation of the detection/total time signal curves (i.e. the time dependence of the total amount of imaging tracer within the reference region VOI containing contributions from all the subsystems) is performed. Additionally the concentrations of the imaging agent in all the compartments and/or subsystems of the identified topology within the VOI under study are determined (panels 11 "All dynamic Parameters", 12 "Free imaging agent in Plasma"; for the amount of imaging agent either as metabolites or unspecifically bound in the tissue or blood volume fractions of the reference region VOI see subpanels 13 "Blood Elements", 14 "Metabolites" and 15 "Reference Tissue unspecific. Binding"; panel 16 is the "Modeled Detection Reference Tissue Signal").

In summary, the final results of this procedure for analysis are
   a. To obtain parametric maps of all relevant dynamic parameters describing the kinetics of the imaging agent within the reference region VOI.
   b. The amount of imaging agent trapped as metabolized products (metabolites) or unspecifically bound in both tissue or blood volume fraction of the target region VOI (see subpanels 13 "Blood Elements", 14 "Metabolites", 15 "Ref Tissue unspecifically bound") are presented either as parametric maps (regional or on a per-voxel basis) or as resulting time depending model curves (for a given VOI).
   c. To obtain the parameter error estimates and all the statistical information (correlation matrix) from the final result of the optimization.
5. Depending on the obtained results about the kinetic of the imaging agent transport within the tissue under study (i.e. from the comparison of the simulations with the time scans) an appropriate development toolkit can be developed (see panel 17 "Clinical Protocols") to obtain efficient clinical protocols (e.g. schedules for injections or taking image data).

In conclusion, the invention relates to a general composite compartmental model (topology) and a compartmental analysis procedure to extract non-invasively the concentration of the free imaging agent in plasma (FIAP), in metabolites and in blood elements (like red cells, platelets, plasma protein etc.) from time signal curves measured within a reference tissue region. This is made possible by deploying an injection function as input to the compartmental analysis. The injection function models the amount of imaging agent administered to the patient as a function of time. This function is determined by the clinical protocol and allows to extract the local free (unmetabolized) imaging agent concentration in plasma by decomposition of the total time signal curves. The procedure is applicable to either the complete set of recorded images (either several static scans or the 4-dim. time-scan data based on a VOI analysis, images which can be reconstructed images from a PET, SPECT, MRI or US scanner) and generates from the input maps of all the relevant chemical, biological and physiological parameters on a per-voxel basis. The invention allows the presentation of the plasma input function to the medical practitioner without the need for invasively drawing blood samples, whereby the plasma input function is determined directly at the position of interest and errors due to differences between the blood samples and the agent at the position of interest are avoided.

Further Aspects and Prerequisites of the Invention are:

Existing reference tissue concepts are extended within a more general framework including labeled metabolites within tissue and blood. Also the penetration of the metabolites through either the blood-tissue barrier within tissues or blood elements is allowed.

The metabolized imaging agent considered can be
(i) nonspecifically bound to non-diffusible binding sites within the tissue and
(ii) diffusible, i.e. agent which leaves the tissue and flows back into the blood being no longer available as free imaging agent. Thus the metabolites within the system are described by an appropriate trapping subsystem which should contain one or more compartments (e.g. within blood, tissue or reference tissue) which under certain conditions can be mathematically lumped together.

The clearance of the labeled metabolites out of the body either from the blood metabolite pool or directly from the tissues under study is considered (see FIG. 1, 700).

All types of metabolites can flow in and out the reference tissue but they cannot be bound within. Also no metabolization of the free imaging agent within the reference tissue should be allowed. Thus a free movement of the metabolites among all reversible subsystems other then the interstitial ones is not allowed (i.e. the metabolites subsystem has no exchange with any other reversible subsystems except the interstitial one).

The imaging agent will be neither specifically bound nor trapped (metabolized) within the reference tissue volume fraction of the VOI under study.

Adaptability to specific clinical examinations via model selection from various libraries containing multiple alternative models (compartmental topology with eventual the corresponding analytical solution, or appropriate composite general solution) for the reference tissue and specification of model parameters (user interactive).

Visualization of the dynamic parameters as parametric maps and of the imaging agent concentrations in all the compartments of the considered model topology as time signal curves with the possibility to fuse the maps representing functional/morphological information with anatomical information.

The invention may be applied in various medical fields, including oncology (hormonal therapy), radio therapy (palliative therapy of bone metastasis, therapy of thyroid), cardiology, neurology, gene expression (immunology and therapy), endocrinology (hormonal malfunction, therapy), nephrology, general pharmacology, hematology, osteology, and toxicology.

Finally it is pointed out that in the present application the term "comprising" does not exclude other elements or steps, that "a" or "an" does not exclude a plurality, and that a single processor or other unit may fulfill the functions of several means. Moreover, reference signs in the claims shall not be construed as limiting their scope.

The invention claimed is:

1. A method for evaluating image data that represent concentration of an imaging agent in a body volume, the method comprising:
determining an injection function ($S_{INJ}(t)$) that models an injection of the imaging agent into a reference region as a function of time;
determining a concentration of free imaging agent in plasma ($C_P$) in the reference region;
determining a time signal in the reference region via convolution and summing using the injection function, the concentration of the free imaging agent in plasma, impulse response functions of blood elements ($G_B$) and metabolites ($G_{MB}$) within a blood volume fraction ($V_B$) of a blood subsystem in the reference region, partial volume fractions of the blood elements ($G_B$) and the metabolites ($G_{MB}$), respectively, within the blood subsystem, impulse response functions of tissue ($G_T$) and metabolites ($G_{MT}$) within a tissue volume fraction ($V_T$) of a reference tissue subsystem in the reference region, and a partial volume fraction of the metabolites ($G_{MT}$) within the reference tissue subsystem, determining the time signal being executed by a processor; and
estimating a distribution of the imaging agent in blood of a patient using the time signal,
wherein the injection function is expressed as a volume flow of the imaging agent through one of a syringe and an infusion system into a vein of the patient.

2. The method of claim 1, further comprising:
evaluating a compartment model of the reference region, the reference region comprising the blood subsystem and the reference tissue subsystem.

3. The method of claim 2, wherein the compartment model comprises compartments for metabolites of the imaging agent in the blood subsystem and the reference tissue subsystem.

4. The method of claim 2, wherein the compartment model comprises compartments for binding of the imaging agent in the blood subsystem and the reference tissue subsystem with binding sites.

5. The method of claim 2, wherein evaluating the compartment model comprises evaluating a target region, in which the imaging agent is specifically bound, based on information obtained from the reference region.

6. The method of claim 2, wherein evaluating the compartment model comprises calculating errors associated with the evaluation of the image data based on different compartment models.

7. The method of claim 2, wherein evaluating the compartment model comprises displaying evaluation results.

8. An examination apparatus, comprising
an imaging system configured to generate image data of the body volume; and
a data processing system configured to perform the method according to claim 1.

9. The examination apparatus of claim 8, wherein the imaging system comprises one of a PET, SPECT, CT, MR or US system.

10. The method of claim 1, wherein the tissue volume fraction comprises interstitial and intracellular volume fractions.

11. A non-transitory computer readable medium that stores programming code, executable by a computer, for evaluating image data that represent concentration of at least one imaging agent in a body volume, the computer readable medium comprising:
injection determining code for determining an ($S_{INJ}(t)$) injection function that models an injection of the imaging agent into a reference region as a function of time;
free imaging agent concentration determining code for determining a concentration of free imaging agent in plasma ($C_P$) in the reference region;
time signal determining code for determining a time signal in the reference region via convolution and summing using the injection function, the concentration of the free imaging agent in plasma, impulse response functions of blood elements ($G_B$) and metabolites ($G_{MB}$) within a blood volume fraction ($V_B$) of a blood subsystem in the reference region, partial volume fractions of the blood elements ($G_B$) and the metabolites ($G_{MB}$), respectively, within the blood subsystem, impulse response functions of tissue ($G_T$) and metabolites ($G_{MT}$) within a tissue volume fraction ($V_B$) of a reference tissue subsystem in the reference region, and a partial volume fraction of the metabolites ($G_{MT}$) within the reference tissue subsystem; and
estimating code for estimating a distribution of the imaging agent in blood of a patient using the time signal, wherein the injection function is expressed as a volume flow of the imaging agent through one of a syringe and an infusion system into a vein of the patient.

12. The non-transitory computer readable medium of claim 11, further comprising:
    evaluating code for evaluating a compartment model of the reference region, the reference region comprising the blood subsystem and the reference tissue subsystem.

13. The non-transitory computer readable medium of claim 12, wherein the compartment model comprises compartments for metabolites of the imaging agent in the blood subsystem and the reference tissue subsystem.

14. The non-transitory computer readable medium of claim 12, wherein the compartment model comprises compartments for binding of the imaging agent in the blood subsystem and the reference tissue subsystem with binding sites.

15. The non-transitory computer readable medium of claim 12, wherein the evaluating code comprises target region code for evaluating a target region, in which the imaging agent is specifically bound, based on information obtained from the reference region.

16. The non-transitory computer readable medium of claim 12, wherein the evaluating code comprises error code for calculating errors associated with the evaluation of the image data based on different compartment models.

17. The non-transitory computer readable medium of claim 12, further comprising display code for displaying evaluation results.

18. The non-transitory computer readable medium of claim 11, wherein the tissue volume fraction comprises interstitial and intracellular volume fractions.

* * * * *